(12) United States Patent
Kraus et al.

(10) Patent No.: US 6,358,216 B1
(45) Date of Patent: Mar. 19, 2002

(54) APPARATUS FOR TAKING MEASUREMENTS IN THE EAR

(75) Inventors: Bernhard Kraus, Braunfels; Elke Kahler, Griesheim; Alexander Klös, Hofheim; Horst Mannebach, Butzbach, all of (DE)

(73) Assignee: Braun Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/335,141

(22) Filed: Jun. 17, 1999

(30) Foreign Application Priority Data

Jan. 19, 1998 (DE) .......................... 198 27 343

(51) Int. Cl.[7] ................................. A61B 5/00
(52) U.S. Cl. ........................... 600/549; 600/559
(58) Field of Search ..................... 600/549, 559; 73/585

(56) References Cited

U.S. PATENT DOCUMENTS

| | | |
|---|---|---|
| 4,567,881 A | 2/1986 | Heller |
| 5,325,863 A | 7/1994 | Pompei |
| 5,419,312 A | 5/1995 | Arenberg |
| 5,673,692 A | 10/1997 | Schulze |
| 5,790,586 A | 8/1998 | Hilton, Jr. |
| 5,919,143 A * | 6/1999 | Jenkins et al. .............. 600/549 |

FOREIGN PATENT DOCUMENTS

| | | |
|---|---|---|
| EP | 0 588 631 | 3/1994 |
| JP | 07286905 | 10/1995 |
| JP | 09005167 | 1/1997 |
| WO | 9623442 | 8/1996 |
| WO | 9801730 | 1/1998 |

OTHER PUBLICATIONS

PCT search report in German.

\* cited by examiner

*Primary Examiner*—Max Hindenburg
(74) *Attorney, Agent, or Firm*—Hopgood, Calimafde, Judlowe & Mondolino LLP

(57) ABSTRACT

The invention is directed to an apparatus for taking measurements in the ear, having a positioning aid enabling a probe head (10) of the apparatus to be properly aligned in a user's auditory canal (12). The apparatus of the present invention comprises a source of radiation (24) emitting energy particularly in the visible region, a photodetector (30) suitable for sensing this radiation, and an associated evaluation unit and, where applicable, an indicating unit for representing the alignment of the probe head in the auditory canal (12). This canal receives the radiation from the radiation source (24), with part of the radiation being scattered back into the probe head (10) and sensed by the photodetector (30). In this arrangement, the radiant power sensed is dependent on the mean distance between the reflecting tissue and the probe head (10), with a minimum radiant power corresponding to a correct alignment of the probe head (10) to the rear auditory canal (12) and hence to the tympanic membrane (38). The output signal of the photodetector (30) preferably controls the frequency and/or volume of an audible signal informing the user of the optimal alignment of the probe head (10), so that the repeat accuracy of the measurement results is improved.

60 Claims, 3 Drawing Sheets

APPARATUS FOR TAKING MEASUREMENTS IN THE EAR

Figure 1:
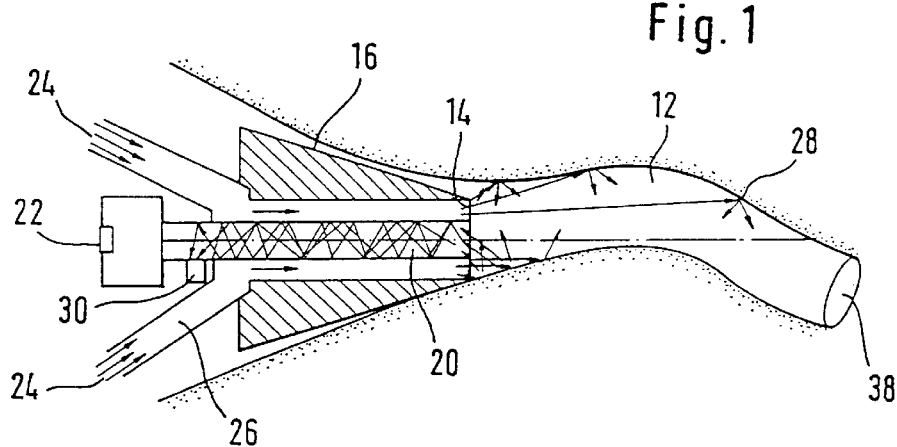

This invention relates to an apparatus for taking measurements in the ear, having a probe head insertable into the ear canal and an indicating unit. Measuring apparatus of this type which include, for example, infrared radiation thermometers or ear reflectometers, are known in the art.

From WO 98/01730 an infrared thermometer having a visual marking system is known, which enables a user during a temperature measurement to maintain a given distance between the probe head and the object of measurement.

However, the art also knows of infrared radiation thermometers for determining the temperature of a human body, whose probe head which is equipped with a radiation inlet is insertable into the ear canal and capable of measuring the infrared radiation emitted by the tympanic membrane. Considering that blood supply to the tympanic membrane is the same as to the temperature center in the brain, this radiation is representative of the true core temperature of the human body.

Because a difference typically exists between the tympanic temperature to be measured and the temperature of the surrounding ear canal tissue, it is necessary for the probe head to be correctly aligned relative to the tympanic membrane for temperature measurement precision. However, this is not always ensured because bends in the ear canal or frequently occurring natural irregularities (exostoses) may block the free view at the tympanic membrane. Hence the measurement result is appreciably affected by the geometry of the respective ear canal so that more or less significant errors may be introduced. Even a subjectively correct seat of the probe head is no guarantee of a correct alignment to the tympanic membrane, because in the worst case a partial obstruction of the radiation inlet by a skin fold is sufficient to make the measured temperature severely dependent on the direction, producing conventionally an erroneous reading not noticeable by the user with a poor repeatability. When the probe head is accidentally placed directly on the ear canal tissue, errors may also be introduced which pretend an excessively low body temperature.

To solve this problem, it is proposed in U.S. Pat. No. 5,325,863 to provide the user with an audible reply indicative of the quality of positioning. Thus the known ear canal thermometer invariably takes several measurements, and it possesses an audible signal detector delivering a tone as the probe head is inserted in the ear canal whenever the measured temperature value is higher than a previous measurement value. In this arrangement, however, the evaluation of the regions whose temperature is sensed depends on chance, and there is no possibility of checking whether the tympanic membrane as the region with the overall highest temperature has been included in the evaluation and the body core temperature correctly detected. Furthermore, errors introduced due to direct placement of the probe head onto tissue cannot be detected and, accordingly, cannot be corrected either when a measurement is taken.

The problems involved in properly aligning the probe head in the ear canal are precisely the same when the impedance of the tympanic membrane is measured using an ear reflectometer capable of determining accumulations of liquid in the tympanum. To this end, sound waves are emitted at different frequencies, and the sound waves reflected by the tympanic membrane are recorded and evaluated.

It is therefore an object of the present invention to provide an apparatus for taking measurements in the ear, with which erroneous readings due to an insufficient alignment of the probe head to the tympanic membrane can be avoided.

According to the present invention, this object is accomplished by an apparatus having a device for determining the alignment of the probe head in the ear canal.

This device comprises a source of radiation emitting electromagnetic radiation to be passed to the measurement spot targeted by the probe head of the apparatus, a detector responding in the corresponding wavelength region for sensing the radiation scattered by the measurement spot, and an evaluation unit arranged downstream of the detector for determining the alignment of the probe head in the ear canal. The device may further include an indicating unit to represent the alignment.

In a preferred embodiment of an apparatus of the present invention, the source of radiation is a light source emitting energy preferably in the visible region or in the near infrared region, the detector then being a photodetector.

To preclude the effects of the radiation passed into the ear canal on the measurement, the mean intensity of the radiation source is selected suitably low so that in particular heating of the ear canal is prevented. This is accomplishable preferably by the use of a pulsed radiation source and a detector circuit synchronized with it. The power consumption of a pulsed radiation source is less than that of a source which is not pulsed, which presents an advantage particularly where battery-powered apparatus are used. In addition, a pulsed radiation source also enables the radiation background to be determined.

An apparatus of the present invention advantageously includes a first radiation guide, in the above embodiment a light guide, which directs the radiation emitted from the radiation source to the measurement spot, that is, the radiation is given off at the end of the radiation guide close to the measurement spot, radiating into the ear canal. The radiation may be focused or, alternatively, it may form a widening radiation cone. Upon striking tissue, the radiation is reflected diffusely, causing part of it to be passed to the detector either via the same or a second radiation guide. The intensity of the radiation sensed by the detector is dependent on the mean distance between the reflecting tissue and the probe head. Therefore, when the probe head is improperly aligned, a relatively high percentage of the radiation, upon diffusion on the walls of the ear canal, is again coupled in the probe head and sensed in the detector, whilst in the presence of a correct alignment of the probe head to the rear auditory canal and the tympanic membrane, only a minimum amount of radiation is sensed. This enables severe erroneous readings to be detected as they may occur, for example, when the probe head is placed directly onto the tissue.

In the above-described use of two radiation guides, the occurrence of indicating errors due to direct overcoupling of the emitted radiation to the detector is precluded.

In another embodiment of a measuring apparatus of the present invention, the first radiation guide is omitted. In this arrangement the radiation source is disposed at the extreme forward end of the probe head.

To instruct the user with regard to a proper alignment of the probe head, it is possible for the probe head alignment to be indicated visually and/or audibly. For this purpose, the device of the present invention measures the amount of diffuse radiation continuously, that is, preferably as early as the moment when the probe head is inserted into the ear canal. Preferably, the indicating unit comprises a device for producing an audible signal whose volume and/or frequency is/are controlled by the output signal of the detector. Shortly upon inserting the probe head into the auditory canal, the user of an apparatus of the present invention receives a direct reply indicative of the optimum alignment of the probe head to the tympanic membrane or at least to the region of the rear auditory canal. This indication causes the user to align the probe head nearly alike for each measurement, so that good repeatability of the measurement results is obtained.

The indicating unit comprises, for example, a voltage-controlled oscillator driven by the output signal of the detector and having a loudspeaker connected thereto. Any variation of the detected radiant power then effects an increase or decrease in the oscillation frequency and/or oscillation amplitude, so that the user hears a correspondingly changing tone when aligning the thermometer in the ear canal. Proper alignment of the probe head is achieved when the tone with the lowest (or highest) frequency and/or amplitude sounds.

To facilitate a measurement by third persons, another embodiment makes provision for the indicating unit to comprise a visual display, in particular an LED line or a pointer instrument providing the user with a visual indication of the proper alignment of the probe head to the rear auditory canal and to the tympanic membrane. This way of representation enables measurements to be taken on sleeping persons without having to disturb them by an audible signal.

In a preferred embodiment, the evaluation unit of an apparatus of the present invention includes the added provision of a threshold value device which activates the indicating unit for the measurement values and/or the indicating unit for representing the alignment not until the radiant power sensed in the detector has fallen below a predetermined threshold value. This enables the indication of a measurement value to be suppressed until the evaluation unit has sensed a satisfactory alignment of the probe head. Still further, the end of measurement can be indicated to the user when the threshold value is reached. The threshold value is fixed at a level ensuring the requisite measurement accuracy also with differently shaped ear canals.

In a particularly advantageous configuration of the measuring apparatus, the threshold value is adapted to the individual diffusivity of the individual ear canal already the moment when the probe head is inserted into the ear canal. This succeeds particularly well when the user initially moves the probe head to and fro in the ear canal, thereby aligning the probe head in different directions. The threshold value device senses the to-and-fro movement by corresponding fluctuations in the output signal of the detector, and it varies the threshold value when the threshold value is not reached within a predetermined measuring period in spite of this movement.

Wrong manipulation by placing the probe head directly on the tissue is assumed to be the case when the output signal of the detector reaches a correspondingly predetermined second threshold value.

Two preferred embodiments of a measuring apparatus of the present invention involve an infrared radiation thermometer having an infrared sensor, particularly for measuring the temperature of the tympanic membrane, and an ear reflectometer having a sound source and a microphone, in particular for measuring the impedance of the tympanic membrane.

Infrared radiation thermometers known in the art typically include a housing with a radiation inlet for the infrared radiation to be measured, and a waveguide extending from the radiation inlet to the infrared sensor. In an infrared radiation thermometer of the present invention, the waveguide serves the function of conveying both the infrared radiation emitted from the tympanic membrane to the infrared sensor and the radiation source's radiation reflected in the auditory canal to the detector. Therefore the infrared sensor and the detector are preferably disposed at the end of the waveguide (which hence also assumes the function of the second radiation guide referred to in the foregoing).

In another aspect, provision is made for two separate radiation guides for passing the infrared radiation and the reflected radiation. Alternatively, it is possible for the infrared radiation needing to be measured, for the emitted radiation and the reflected radiation to be guided in a single radiation guide. It is also possible to substitute an optic system having lenses and/or mirrors for the radiation guide (s).

The detector is preferably arranged laterally in the end area of the waveguide in order to minimize its effect on the viewing angle and the sensitivity of the infrared sensor. However, the detector may also be integrated in the housing of the infrared sensor in which case the window material of the sensor housing is selected so that the window is transmissive both to the infrared radiation and in the wavelength region utilized by the radiation source. In a particular configuration, the detector with the infrared sensor is integrated in a microsystem on a chip. Similarly, an integration of infrared sensor, detector and radiation source on a chip or in a housing is also possible.

In an ear reflectometer of the present invention, the detector and the microphone may have a common housing. In a particular configuration, the detector and the microphone are integrated in a microsystem on a chip. Similarly, an integration of microphone, detector and radiation source on a chip or in a housing is also possible.

Figure 2:
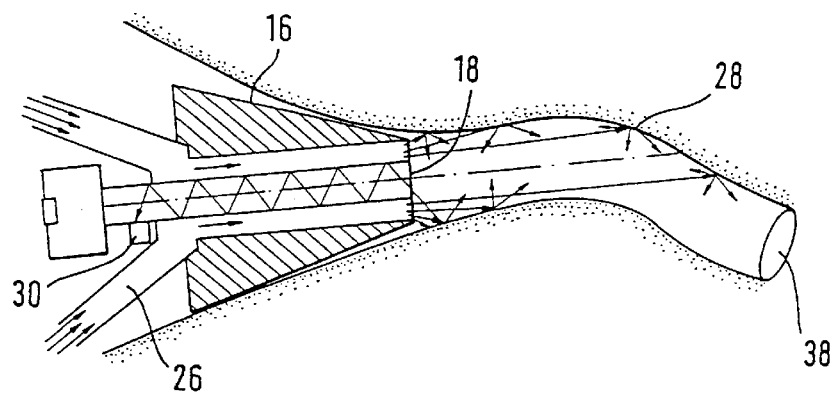
Figure 3:
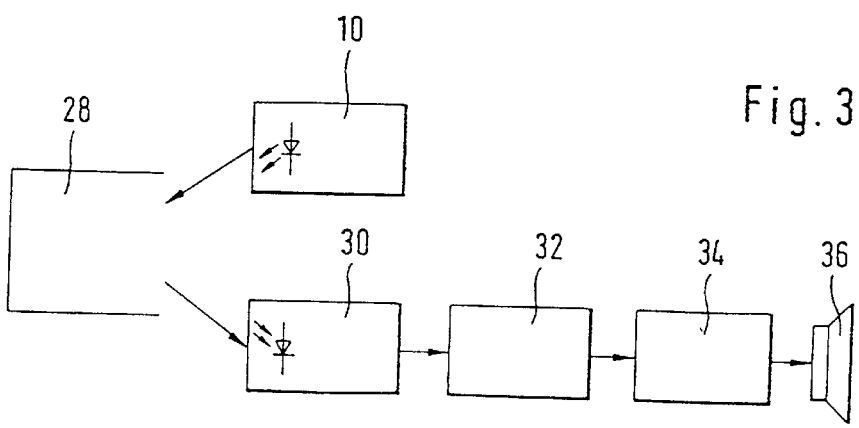
Figure 4:
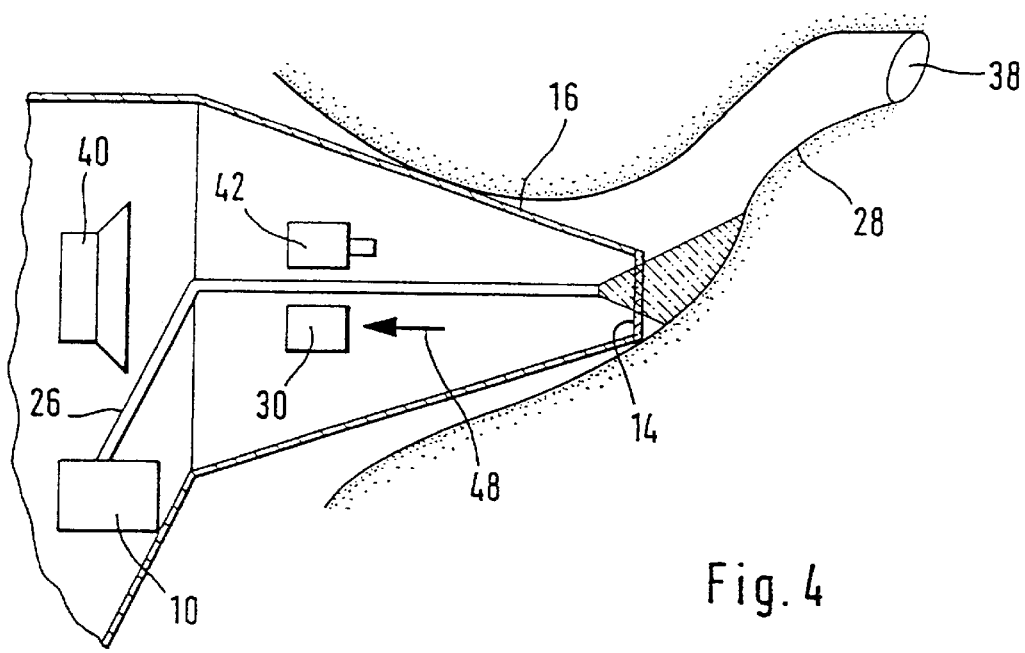
Figure 5:
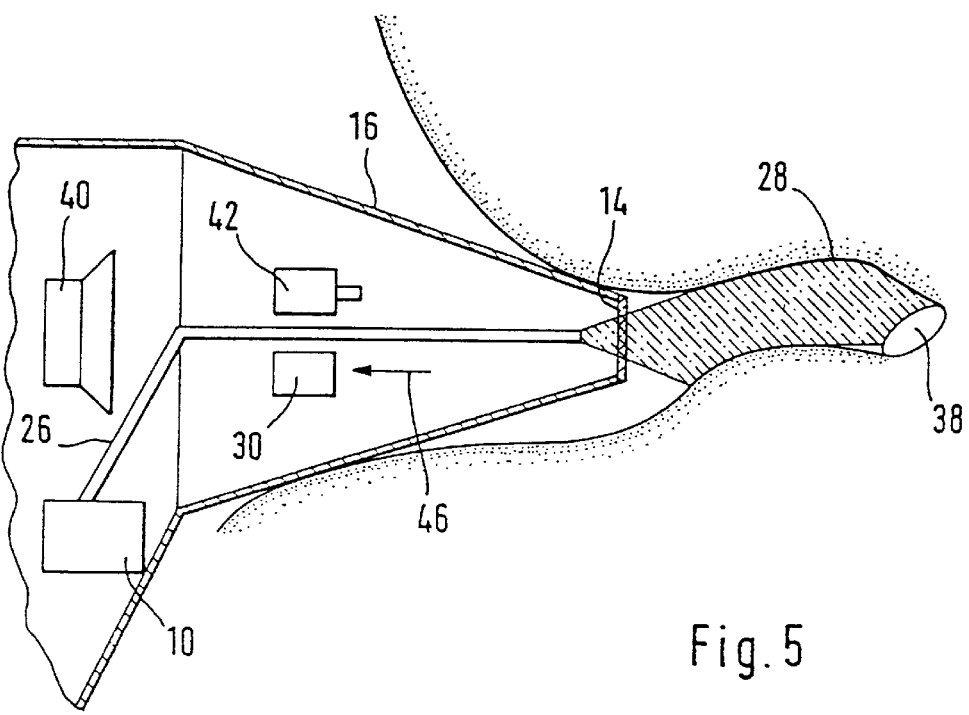

The present invention will be described in the following with reference to preferred embodiments in connection with the accompanying drawing. Further embodiments are dealt with in the description. The drawing shows schematically in FIG. 1 a probe head of an infrared radiation thermometer of the present invention which is improperly aligned in a user's auditory canal;

FIG. 2 the probe head of FIG. 1 but properly aligned;

FIG. 3 the components of the device of the present invention for determining the alignment of the probe head of an infrared radiation thermometer;

FIG. 4 a probe head of an ear reflectometer of the present invention which is improperly aligned in a user's auditory canal;

FIG. 5 the probe head of FIG. 4 but properly aligned; and

Figure 6:
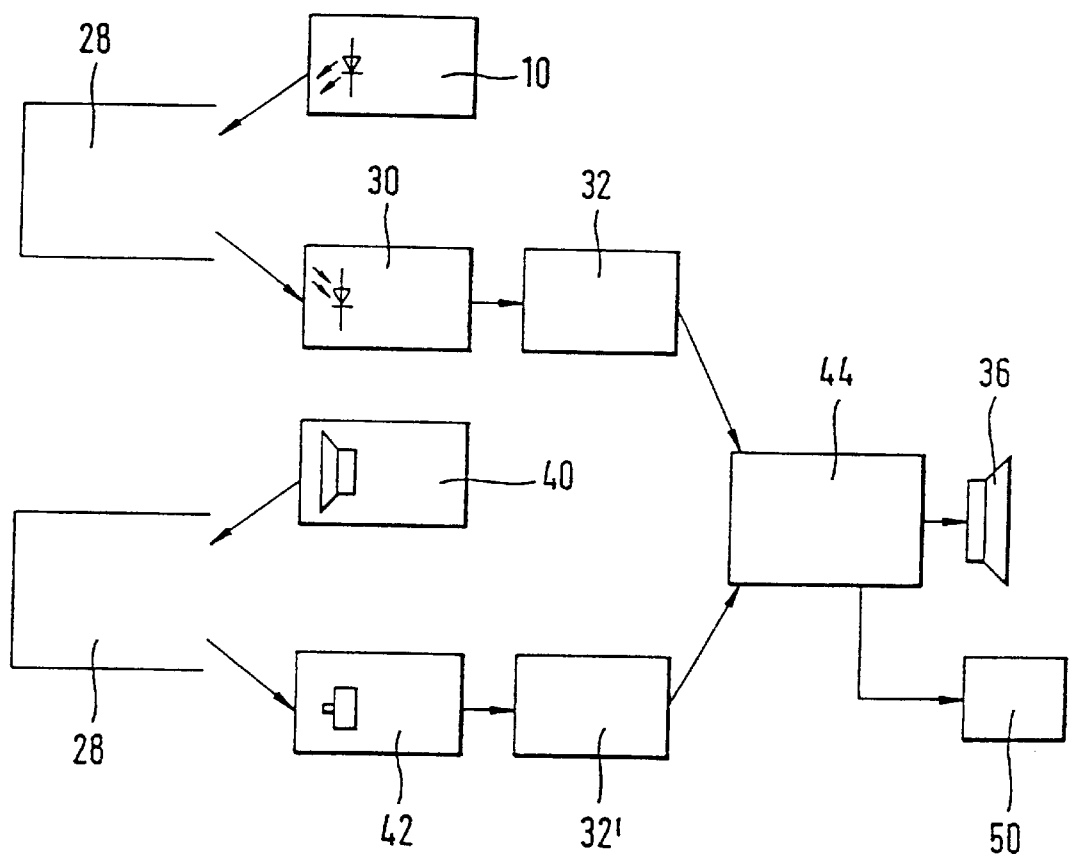

FIG. 6 the components of the device of the present invention for determining the alignment of the probe head and the components for the ear reflectometry.

FIGS. 1 and 2 show schematically a probe head of an infrared radiation thermometer of the present invention as introduced into a user's ear canal 12 for taking the patient's temperature. As is known, the probe head comprises a housing 16 tapering conically in the direction of a radiation inlet 14 for the infrared radiation needing to be measured. The radiation inlet 14 is sealed by a radiation inlet window 18 to protect the interior of the housing from contamination and damage.

The forward end of the probe head may be covered by an exchangeable protective cover (not shown) to prevent in particular cross contamination between patients. It is made, for example, from a thin foil of polyethylene material.

The infrared radiation incident in the radiation inlet 14 is conveyed in a manner known in the art through a waveguide 20 to an infrared sensor 22. The infrared sensor 22 is connected to an electronic evaluation unit (not shown)

which converts the sensed infrared radiation into temperature information indicated by means of an indicating unit (not shown either) for the measurement values.

In addition, the probe head comprises according to the present invention a device for determining the alignment of the probe head in the ear canal, said device including a light source 10 (FIG. 3) emitting light, for example, in the visible range or in the near infrared, which light 24 is directed through a first radiation guide 26 surrounding the waveguide 20 concentrically to the radiation inlet 14. From there it radiates upon the ear canal 12 and is diffusely reflected by the ear canal's walls 28, as illustrated by arrows in the Figures. Part of this diffuse radiation is coupled back into the probe head through the radiation inlet 14 and directed, through the waveguide 20, to a photodetector 30 disposed laterally in the rear part of the waveguide 20 and issuing a corresponding electrical signal. This signal is delivered to an evaluation unit (not shown) and, in an alternative embodiment, also to an indicating unit presenting visual and/or audible information to the user about the alignment of the probe head in the ear canal in the manner subsequently described. In another embodiment, the first radiation guide 26 is at least partially disposed in the waveguide 20.

In order to preclude an appreciable heating of the ear canal 12 and an attendant effect on the temperature measurement, the mean intensity of the light 24 radiated into the ear canal 12 is selected correspondingly low. To this end, the light source 10 is operated in the pulse mode in a manner known in the art, and the photodetector 30 is synchronized with it.

In another embodiment, the photodetector 30 is arranged in the housing of the infrared sensor 22, with the window material of the sensor housing being selected such as to be transmissive to both the infrared radiation needing to be measured and the light 24 emitted by the light source 10. In a further configuration, the infrared sensor 22 and the photodetector 30 are integrated in a microsystem on a chip. In other variants, the light source 10 with the infrared sensor and/or detector are integrated on a chip or arranged in a housing.

In a further embodiment not illustrated in the Figures, the light coupled into the radiation inlet 14 of the probe head, rather than being conveyed through the waveguide 20, is conveyed through an additional radiation guide to the photodetector 30 in order to avoid that the field of view of the infrared sensor 22 is possibly affected by the photodetector 30.

Because the light 24 emitted from the light source 10 in the probe head is conveyed in the first radiation guide 26 separately from the radiation emitted from the ear canal in the waveguide 20, it is ensured that light emitted from the light source and reflected at the radiation inlet window 18 or at the protective cover (not shown) is prevented from reaching the photodetector 30. Therefore, even in the event of wrong manipulation of the clinical infrared thermometer of the present invention due to direct placement of the probe head upon tissue, its transparency to the light emitted by the light source operates to couple back to the photodetector 30 only light reflected on the tissue in sufficient intensity, so that any misalignment of the probe head can be detected and avoided.

Because the light radiated into the ear canal 12 is reflected there diffusely, the intensity of the radiation sensed by the photodetector 30 is dependent on the mean distance between the probe head and the ear canal 12. When the probe head is misaligned as illustrated, for example, in FIG. 1, a relatively high percentage of the light radiated into the ear canal, following diffusion on the walls 28 of the ear canal 12, is coupled back into the probe head to be sensed in the photodetector 30. By contrast, with the probe head properly aligned in the ear canal 12 as illustrated in FIG. 2, only a small percentage of the light scattered on the walls 28 of the ear canal 12 is sensed in the photodetector 30. In this event, the probe head of the infrared thermometer is directed toward the rear ear canal 12 and the tympanic membrane 38 so that the infrared sensor 22 receives predominantly the radiation from the tympanic membrane and the user's correct body core temperature is measured.

As illustrated schematically in FIG. 3, the radiation source 10 emits radiation which is scattered on the walls 28 of the ear canal and is passed at least in part to the detector 30 whose output signal is amplified in an amplifier 32 and supplied to a voltage-controlled oscillator (VCO) 34. The output signal of the oscillator 34 is converted into an audible signal via a loudspeaker 36. Considering that a higher detected radiant power results in a higher-level signal of the photodetector 30, a correspondingly different oscillation frequency of the oscillator results as well. The user, in moving the probe head in his ear to and fro, then hears a tone of a higher and lower loudness level which is attributable to the resultant variation of the radiant power measured. The correct alignment of the probe head shown in FIG. 2 is achieved when the tone with the lowest or highest frequency sounds.

On any variation of the alignment of the probe head in the ear the user thus receives a direct audible response enabling him to properly align the probe head to the rear area of the auditory canal 12, whose temperature corresponds to the temperature of the tympanic membrane 38 or departs from this temperature only a small amount. The device of the present invention thus assists the user in finding the correct alignment of the probe head in the ear canal and ensures, independently of the individual size and shape of the ear canal, an optimum alignment of the probe head for each measurement so that a good repeat accuracy of the measurement results is obtained.

FIGS. 4 and 5 illustrate schematically a probe head of an ear reflectometer equipped with a device of the present invention for determining the alignment of the probe head inserted into an ear canal. The probe head is of a structure similar to the one illustrated in FIGS. 1 and 2, substituting however in a manner known in the art a sound source 40 and a microphone 42, which are both aligned in the direction of a radiation inlet 14, for the infrared sensor 22. Moreover, this probe head does not have a waveguide 20 but only the first radiation guide 26 through which radiation emitted from the light source 10 is guided to the radiation inlet 14. In another embodiment of the present invention, provision is made for a second radiation guide through which radiation reflected from the ear canal is passed to the detector 30. Alternatively, the emitted and reflected radiation may be guided in a single radiation guide. Otherwise in FIGS. 4, 5 and 6 the same reference characters are applied to like parts as those used in the FIGS. 1, 2 and 3 so that these need not be described again.

FIG. 4 shows schematically a probe head improperly positioned in the ear canal, as a result of which the detector 30 senses a reflected radiation of correspondingly high intensity illustrated symbolically by a thick arrow 48, whilst FIG. 5 shows a probe head in proper alignment whose detector 30 senses only a comparatively low radiant power illustrated symbolically by a thin arrow 46.

As shown schematically in FIG. 6, in an ear reflectometer of the present invention a processor 44 is used for processing both the output signal of the amplifier 32 arranged downstream of the detector 30 and the output signals of the microphone 42 which are amplified in an amplifier 32'. The result of the reflectance measurement is preferably shown on a display 50 connected to the processor 44.

What is claimed is:

1. An apparatus for taking measurements in the ear having a probe head insertable into the ear canal and an indicating unit for measured values, wherein the apparatus includes a device for determining the alignment of the probe head in the ear canal.

2. The apparatus as claimed in claim 1, wherein further includes an indicating unit to represent the alignment of the probe head in the ear canal.

3. The apparatus as claimed in claim 1 wherein the device for determining the alignment comprises the following components: a source of radiation (10) for radiating electromagnetic radiation of a given wavelength onto the measurement spot; a detector (30) for sensing the radiation scattered by the measurement spot; and an evaluation unit arranged downstream of the detector (30) for determining the alignment of the probe head in the ear canal.

4. The apparatus as claimed in claim 3, wherein the evaluation unit includes a threshold value device which activates one or both indicating units not until the output signal of the detector (30) has exceeded or fallen below a predetermined threshold value.

5. The apparatus as claimed in claim 4, wherein the threshold value is adapted to be varied by the threshold value device.

6. The apparatus as claimed in claim 3, wherein the source of radiation (10) is a light source, and the detector is a photodetector (30).

7. The apparatus as claimed in claim 3, wherein the radiation source (10) emits pulsed radiation, and the detector (30) is synchronized with the radiation source (10).

8. The apparatus as claimed in claim 3, wherein it includes a radiation guide, in particular a light guide (26), for the radiation emitted from the radiation source (10).

9. The apparatus as claimed in claim 3, wherein it includes a radiation guide, in particular a light guide (20), for the radiation emitted from the measurement spot.

10. The apparatus as claimed in claim 2, wherein the indicating unit for representing the alignment comprises a device for producing an audible signal whose volume and/or frequency is/are controlled by the output signal of a detector (30) for sensing radiation scattered by the measurement spot.

11. The apparatus as claimed in claim 2, wherein the indicating unit comprises a visual display, in particular an LED line or a pointer instrument.

12. The apparatus as claimed in claim 1, wherein it is an infrared radiation thermometer having an infrared sensor (22), particularly for measuring the temperature of the tympanic membrane, or an ear reflectometer having a sound source (40) and a microphone (42), in particular for measuring the impedance of the tympanic membrane.

13. The infrared radiation thermometer as claimed in claim 12, wherein a detector (30) for sensing radiation scattered by the measurement spot and the infrared sensor (22) are disposed at the end of a second radiation guide (20).

14. The infrared radiation thermometer as claimed in claim 12, wherein a detector (30) for sensing radiation scattered by the measurement spot and the infrared sensor (22) have a common housing.

15. The infrared radiation thermometer as claimed in claim 12, wherein a detector (30) for sensing radiation scattered by the measurement spot and the infrared sensor (22) are integrated on the same chip.

16. The infrared radiation thermometer as claimed in claim 12, wherein a detector (30) for sensing radiation scattered by the measurement spot and the microphone (42) have a common housing.

17. The infrared radiation thermometer as claimed in claim 12, wherein a detector (30) for sensing radiation scattered by the measurement spot and the microphone (42) are integrated on te same chip.

18. The apparatus as claimed in claim 14, wherein the radiation source (10) is arranged in the same housing as the detector (30).

19. The apparatus as claimed in claim 14, wherein the radiation source (10) is integrated on the same chip as the detector.

20. The apparatus as claimed in claim 2, wherein the device for determining the alignment comprises the following components: a source of radiation (10) for radiating electromagnetic radiation of a given wavelength onto the measurement spot; a detector (30) for sensing the radiation scattered by the measurement spot; and an evaluation unit arranged downstream of the detector (30) for determining the alignment of the probe head in the ear canal.

21. The apparatus as claimed in claim 4, wherein the source of radiation (10) is a light source, and the detector is a photodetector (30).

22. The apparatus as claimed in claim 5, wherein the source of radiation (10) is a light source, and the detector is a photodetector (30).

23. The apparatus as claimed in claim 4, wherein the radiation source (10) emits pulsed radiation, and the detector (30) is synchronized with the radiation source (10).

24. The apparatus as claimed in claim 5, wherein the radiation source (10) emits pulsed radiation, and the detector (30) is synchronized with the radiation source (10).

25. The apparatus as claimed in claim 6, wherein the radiation source (10) emits pulsed radiation, and the detector (30) is synchronized with the radiation source (10).

26. The apparatus as claimed in claim 4, wherein it includes a radiation guide, in particular a light guide (26), for the radiation emitted from the radiation source (10).

27. The apparatus as claimed in claim 5, wherein it includes a radiation guide, in particular a light guide (26), for the radiation emitted from the radiation source (10).

28. The apparatus as claimed in claim 6, wherein it includes a radiation guide, in particular a light guide (26), for the radiation emitted from the radiation source (10).

29. The apparatus as claimed in claim 7, wherein it includes a radiation guide, in particular a light guide (26), for the radiation emitted from the radiation source (10).

30. The apparatus as claimed in claim 4, wherein it includes a radiation guide, in particular a light guide (20), for the radiation emitted from the measurement spot.

31. The apparatus as claimed in claim 5, wherein it includes a radiation guide, in particular a light guide (20), for the radiation emitted from the measurement spot.

32. The apparatus as claimed in claim 6, wherein it includes a radiation guide, in particular a light guide (20), for the radiation emitted from the measurement spot.

33. The apparatus as claimed in claim 7, wherein it includes a radiation guide, in particular a light guide (20), for the radiation emitted from the measurement spot.

34. The apparatus as claimed in claim 8, wherein it includes a radiation guide, in particular a light guide (20), for the radiation emitted from the measurement spot.

35. The apparatus as claimed in claim 3, wherein the indicating unit for representing the alignment comprises a device for producing an audible signal whose volume and/or frequency is/are controlled by the output signal of the detector (30).

36. The apparatus as claimed in claim 4, wherein the indicating unit for representing the alignment comprises a device for producing an audible signal whose volume and/or frequency is/are controlled by the output signal of the detector (30).

37. The apparatus as claimed in claim 5, wherein the indicating unit for representing the alignment comprises a device for producing an audible signal whose volume and/or frequency is/are controlled by the output signal of the detector (30).

38. The apparatus as claimed in claim 6, wherein the indicating unit for representing the alignment comprises a device for producing an audible signal whose volume and/or frequency is/are controlled by the output signal of the detector (30).

39. The apparatus as claimed in claim 7, wherein the indicating unit for representing the alignment comprises a device for producing an audible signal whose volume and/or frequency is/are controlled by the output signal of the detector (30).

40. The apparatus as claimed in claim 8, wherein the indicating unit for representing the alignment comprises a device for producing an audible signal whose volume and/or frequency is/are controlled by the output signal of the detector (30).

41. The apparatus as claimed in claim 9, wherein the indicating unit for representing the alignment comprises a device for producing an audible signal whose volume and/or frequency is/are controlled by the output signal of the detector (30).

42. The apparatus as claimed in claim 3, wherein the indicating unit comprises a visual display.

43. The apparatus as claimed in claim 4, wherein the indicating unit comprises a visual display.

44. The apparatus as claimed in claim 2, wherein it is an infrared radiation thermometer having an infrared sensor (22), particularly for measuring the temperature of the tympanic membrane, or an ear reflectometer having a sound source (40) and a microphone (42), in particular for measuring the impedance of the tympanic membrane.

45. The apparatus as claimed in claim 3, wherein it is an infrared radiation thermometer having an infrared sensor (22), particularly for measuring the temperature of the tympanic membrane, or an ear reflectometer having a sound source (40) and a microphone (42), in particular for measuring the impedance of the tympanic membrane.

46. The apparatus as claimed in claim 4, wherein it is an infrared radiation thermometer having an infrared sensor (22), particularly for measuring the temperature of the tympanic membrane, or an ear reflectometer having a sound source (40) and a microphone (42), in particular for measuring the impedance of the tympanic membrane.

47. The infrared radiation thermometer as claimed in claim 13 wherein the detector (30) and the infrared sensor (22) have a common housing.

48. The infrared radiation thermometer as claimed in claim 13 wherein the detector (30) and the infrared sensor (22) are integrated on the same chip.

49. The infrared radiation thermometer as claimed in claim 14 wherein the detector (30) and the infrared sensor (22) are integrated on the same chip.

50. The ear reflectometer as claimed in claim 16 wherein the detector (30) and the microphone (42) are integrated on the same chip.

51. The apparatus as claimed in claim 15, wherein the radiation source (10) is arranged in the same housing as the detector (30).

52. The apparatus as claimed in claim 16, wherein the radiation source (10) is arranged in the same housing as the detector (30).

53. The apparatus as claimed in claim 17, wherein the radiation source (10) is arranged in the same housing as the detector (30).

54. The apparatus as claimed in claim 15, wherein radiation source (10) is integrated on the same chip as the detector.

55. The apparatus as claimed in claim 16, wherein radiation source (10) is integrated on the same chip as the detector.

56. The apparatus as claimed in claim 17, wherein radiation source (10) is integrated on the same chip as the detector.

57. The apparatus as claimed in claim 18, wherein radiation source (10) is integrated on the same chip as the detector.

58. The apparatus as claimed in claim 42, wherein the indicating unit comprises an LED line or pointer instrument.

59. The apparatus as claimed in claim 43, wherein the indicating unit comprises an LED line or pointer instrument.

60. An apparatus for taking measurements in the ear, comprising a probe head insertable into the ear canal, an indicating unit for indicating measured values, and a device for determining and/or indicating the alignment of the probe head in the ear canal, wherein said determining and/or indicating the alignment is provided prior to taking a measurement.

* * * * *